United States Patent
Schall et al.

(10) Patent No.: US 10,724,060 B2
(45) Date of Patent: Jul. 28, 2020

(54) ENHANCEMENT OF LIGNOCELLULOSE SACCHARIFICATION VIA A LOW TEMPERATURE IONIC LIQUID PRE-TREATMENT SCHEME

(71) Applicant: The University of Toledo, Toledo, OH (US)

(72) Inventors: Constance A. Schall, Sylvania, OH (US); Samira Vasheghani Farahani, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/119,487

(22) PCT Filed: Feb. 16, 2015

(86) PCT No.: PCT/US2015/016019
§ 371 (c)(1),
(2) Date: Aug. 17, 2016

(87) PCT Pub. No.: WO2015/123627
PCT Pub. Date: Aug. 20, 2015

(65) Prior Publication Data
US 2017/0009265 A1    Jan. 12, 2017

Related U.S. Application Data

(60) Provisional application No. 61/940,542, filed on Feb. 17, 2014.

(51) Int. Cl.
*C12P 19/02* (2006.01)
*C08B 37/00* (2006.01)
*C08H 8/00* (2010.01)
*C12P 19/14* (2006.01)
*C13K 1/02* (2006.01)
*C08H 7/00* (2011.01)
*C13K 13/00* (2006.01)
*C12N 9/42* (2006.01)

(52) U.S. Cl.
CPC .......... *C12P 19/02* (2013.01); *C08B 37/0057* (2013.01); *C08H 6/00* (2013.01); *C08H 8/00* (2013.01); *C12P 19/14* (2013.01); *C13K 1/02* (2013.01); *C13K 13/002* (2013.01); *C12N 9/2437* (2013.01); *C12P 2201/00* (2013.01)

(58) Field of Classification Search
None
See application file for complete search history.

(56) References Cited

U.S. PATENT DOCUMENTS

| | | | | |
|---|---|---|---|---|
| 2010/0298611 A1* | 11/2010 | Parekh | ..................... | C12N 1/22 568/840 |
| 2012/0193046 A1* | 8/2012 | Varanasi | ................... | C12P 7/10 162/9 |

* cited by examiner

*Primary Examiner* — Paul J Holland
(74) *Attorney, Agent, or Firm* — MacMillan, Sobanski & Todd, LLC

(57) ABSTRACT

A method for pretreating lignocellulosic biomass having a lignin component, a hemicellulose component, and a cellulose component, for conversion to sugar is disclosed. Also disclosed is the pretreated lignocellulosic biomass resulting from the method.

34 Claims, 9 Drawing Sheets
(8 of 9 Drawing Sheet(s) Filed in Color)

ENHANCEMENT OF LIGNOCELLULOSE SACCHARIFICATION VIA A LOW TEMPERATURE IONIC LIQUID PRE-TREATMENT SCHEME

RELATED APPLICATIONS

This application claims priority to U.S. Provisional Application Ser. No. 61/940,542, filed under 35 U.S.C. § 111(b) on Feb. 17, 2014, the disclosure of which is incorporated herein by reference in its entirety.

STATEMENT REGARDING FEDERALLY SPONSORED RESEARCH

This invention was made with government support under Grant Number 0933250 awarded by the National Science Foundation. The government has certain rights in the invention.

BACKGROUND OF THE INVENTION

Lignocellulosic biomass, also referred to as biomass, includes waste materials such as corn stover, sawdust, straws, bagasse, municipal solid waste (paper and cardboard), and dedicated lignocellulose crops such as poplar, *miscanthus*, and switchgrass. These agricultural and waste materials are being developed as alternate domestic sources for production of carbon-based products such as fuels, chemicals, and the like. Lignocellulosic biomass is an attractive feedstock because it is an abundant, domestic, renewable source that can be converted to carbon-based chemicals or liquid transportation fuels.

Terrestrial biomass (lignocellulosic material) is composed of three major components: cellulose (30-50%), a highly crystalline polymer of cellobiose (a glucose dimer); hemicellulose (15-30%), a complex amorphous polymer of five-(pentose) and six-(hexose) carbon sugars; and lignin (5-30%), a highly cross-linked amorphous polymer of phenolic compounds. Lignin is a polyphenyl propanoid macromolecular assembly that is covalently cross-linked to hemicellulose. These components of biomass can serve as a source of carbon-based feedstock for fuel and chemical production in much the same way that crude oil serves as the carbon feedstock in petrochemical refineries. Cellulose and hemicellulose are the major polysaccharide components which, when hydrolyzed into their sugars, can be converted into ethanol or butanol fuel, polymer precursors such as 1,3-propanediol, lactic acid, or other products through various fermentation methods. These sugars also form the feedstock for production of a variety of chemicals and polymers through chemical conversion or fermentation. However, the complex and compact structure of lignocellulosic biomass renders this feedstock largely impenetrable to water, catalysts, or enzymes used to hydrolyze its constituent polysaccharides to monomeric sugars (saccharification).

In its natural state, cellulose is highly crystalline in structure with individual cellulose polymer chains held together by a strong hydrogen bonding network and van der Waals forces. The individual cellulose chains are linear condensation polymer molecules of anhydroglucose units covalently linked by β-1,4 glycosidic bonds with degrees of polymerization (dp) ranging from, typically, 1,000 to 15,000 units. The high crystallinity of cellulose, while imparting structural integrity and mechanical strength to the material, renders it recalcitrant towards hydrolysis aimed at producing glucose (which is a feedstock for producing fuels and chemicals) from this polysaccharide.

In lignocellulosic biomass, crystalline cellulose fibrils are embedded in a less well-organized hemicellulose matrix which, in turn, is linked to lignin. Hydrolysis of cellulose and hemicellulose polysaccharides into their monomeric sugars, glucose, xylose, and other sugars, provides the basic precursors useful for producing fuels (i.e., ethanol or butanol) and chemicals from biomass via the sugar platform. However, biomass is not easily penetrated by water or enzymes and must be pretreated to realize high yields of sugars during enzymatic hydrolysis of the polysaccharides. Enzyme hydrolysis is often favored over mineral acid-catalyzed hydrolysis since mineral acids produce sugar degradation products such as hydroxymethyl furfural (HMF), furfural, levulinic acid, and formic acid. These sugar degradation products are inhibitory to downstream fermentation steps.

Due to the structural complexity of lignocellulosic biomass and the inaccessibility of biomass polysaccharides to water and catalysts, hydrolysis rates to the monomeric sugars that form the sugar platform are extremely slow. Proper pretreatment of the biomass is therefore required to enable efficient saccharification of the cellulose and hemicellulose components to their constituent sugars. The pretreatment generally required for biomass is more severe than that required for starch-based (i.e. corn grain) ethanol production. The hydrolysis of biomass polysaccharides (cellulose and hemicellulose) also requires a complex mixture of enzymes (cellulases and hemicellulases) due to the heterogeneity of hemicellulose and the crystalline nature of cellulose in contrast to the less complex amorphous structure of starch-based feedstocks (amylose). Effective pretreatment and hydrolysis (saccharification) of biomass present key challenges in the development of sustainable processes for chemical and fuel production from biomass. Current pretreatment approaches suffer from slow reaction rates of cellulose and hemicellulose hydrolysis (using cellulases and hemicellulases), low sugar yields, and degradation of biomass or pretreatment chemicals due to the severity of the current pretreatment processes.

Furthermore, enzymatic access to cellulose, for hydrolysis, is restricted by hemicellulose and lignin. Neither the water molecules nor the catalysts for hydrolysis (saccharification) are able to easily penetrate the crystalline matrix of cellulose. As a remedy, slow reaction rates have been increased by pretreatment involving an ionic liquid incubation of the biomass, which is capable of partially dissolving the cellulosic and hemicellulosic portion at various temperatures ranging between about 120° C. and about 160° C., and resulting in higher digestibility yields. However, the high temperature incubation is not favorable from an energy input standpoint. High temperatures can also lead to degradation of the feedstock and ionic liquid, as well as the promotion of unwanted side reactions. Thus, there remains a need for efficient methods of enhancing saccharification of cellulose and hemicellulose from biomass for fuel and chemical production that do not require high temperatures.

SUMMARY OF THE INVENTION

Provided herein is a method of pretreating lignocellulosic biomass having a lignin component, a hemicellulose component, and a cellulose component, for conversion to sugar, the method comprising contacting the biomass with an oxidizing agent at a first temperature for a first period of time sufficient to at least partially remove or decompose the lignin component, thereby producing LOX biomass; contacting the LOX biomass with an ionic liquid at a second temperature for a second period of time, thereby producing a first mixture comprising IL and LOX biomass; contacting the first mixture with a solvent, thereby producing a second mixture comprising LOXIL-treated biomass and solvent, wherein the IL is substantially soluble in the solvent and at least one of the cellulose component or the hemicellulose component is substantially insoluble in the solvent; and separating the LOXIL-treated biomass from the solvent to produce pretreated lignocellulosic biomass.

In certain embodiments, the lignocellulosic biomass comprises poplar, corn stover, switchgrass, agricultural or forest wastes, other lignocellulosic biomass sources, or a combination thereof.

In certain embodiments, the separating comprises mixing the second mixture so as to precipitate the LOXIL-treated biomass from the IL. In particular embodiments, the method further comprises the step of washing the precipitated LOXIL-treated biomass with the solvent so as to displace the IL. In particular embodiments, the method further comprises removing liquid from the precipitated LOXIL-treated biomass through filtration. In certain embodiments, the method further comprises the step of contacting the pretreated lignocellulosic biomass with enzymes capable of hydrolyzing at least one of cellulose or hemicellulose, and converting at least one of the cellulose component or the hemicellulose component to hexose and/or pentose sugars. In certain embodiments, the enzymes comprise a mixture of cellulases and/or hemicellulases.

In certain embodiments, the method further comprises the step of contacting the second mixture with an acid catalyst to hydrolyze at least one of the hemicellulose component or cellulose component. In certain embodiments, the method further comprises the step of contacting the pretreated lignocellulosic biomass with enzymes capable of hydrolyzing at least one of cellulose or hemicellulose, and converting at least one of the cellulose component or the hemicellulose component to hexose and/or pentose sugars. In certain embodiments, the enzymes comprise a mixture of cellulases and/or hemicellulases.

In certain embodiments, the first period of time ranges from about 1 hour to about 48 hours. In certain embodiments, the first temperature ranges from about 18° C. to about 40° C. In certain embodiments, the oxidizing agent is combined in an alkaline solution. In particular embodiments the alkaline component is derived from CaO, Ca(OH)$_2$, NH$_4$OH or NaOH. In particular embodiments, the alkaline oxidizing solution comprises NaOH and H$_2$O$_2$. In certain embodiments, the alkaline oxidizing solution is mixed with the biomass at a NaOH-to-biomass ratio of about 10 wt %, and a H$_2$O$_2$-to-biomass ratio of about 12.5 wt %. In certain embodiments, the oxidizing agent is selected from the group consisting of: hydrogen peroxide, calcium hypochlorite, chlorine dioxide, ozone, potassium peroxymonosulfate, and ammonium persulfate.

In certain embodiments, the second temperature ranges from about 20° C. to about 75° C. In certain embodiments, the second period of time ranges from about 1 hour to about 24 hours.

In certain embodiments, the LOX biomass is at least partially dried prior to being contacted with the ionic liquid. In certain embodiments, the LOX biomass is filtered prior to being contacted with the ionic liquid.

In certain embodiments, the ionic liquid comprises a cation selected from the group consisting of: imidazolium, pyrroldinium, pyridinium, phosphonium, and ammonium. In certain embodiments, the ionic liquid has the structural formula of Formula I:

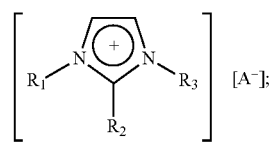

Formula I wherein each of $R_1$, $R_2$, and $R_3$ is independently hydrogen, an alkyl group having 1 to 8 carbon atoms, an alkoxy group having 1 to 8 carbon atoms, or an alkene group having 2 to 8 carbon atoms, and A is a halide, acetate, formate, dicyanamide, carboxylate, or phosphate anion. In particular embodiments, the alkyl group is substituted with sulfone, sulfoxide, thioether, ether, amide, or amine. In particular embodiments, the alkene group is an allyl or vinyl group. In particular embodiments, the halide is a chloride, fluoride, bromide, or iodide. In certain embodiments, the ionic liquid consists essentially of 1-ethyl-3-methylimidazolium acetate. In certain embodiments, the ionic liquid consists essentially of 1-n-butyl-3-methylimidazolium chloride. In certain embodiments, the ionic liquid consists essentially of 1-allyl-3-methyl imidazolium chloride or allyl-imidazlium chloride. In certain embodiments, the ionic liquid consists essentially of 3-methyl-N-butylpyridinium chloride.

In certain embodiments, the solvent is selected from the group consisting of: water, ethanol, methanol, and acetonitrile.

In certain embodiments, the method further comprises the step of washing the LOXIL-treated biomass with a second solvent, wherein at least one of the cellulose component or the hemicellulose component is substantially insoluble in the second solvent, and the IL is substantially soluble in the second solvent. In particular embodiments, the washing fractionates and separates the cellulose component and the hemicellulose component. In particular embodiments, the second solvent is selected from the group consisting of: water, ethanol, methanol, and acetonitrile.

In certain embodiments, the method further comprises the step of recovering the IL by at least one of: distillation, membrane separation, solid phase extraction, or liquid-liquid extraction.

In certain embodiments, the contacting of the biomass with the oxidizing agent comprises combining the biomass with an oxidizing solution at about 10% (w/w) solids loading. In particular embodiments, the method further comprises the step of mixing the combination of biomass and oxidizing solution.

In certain embodiments, the contacting of the LOX biomass with the ionic liquid comprises combining the LOX biomass with the ionic liquid at a range of from about 5% to about 20% (w/w) solids loading. In particular embodiments, the method further comprises the step of mixing the combination of LOX biomass and ionic liquid.

Further provided is the pretreated lignocellulosic biomass produced from the method described herein.

BRIEF DESCRIPTION OF THE DRAWING

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 2A is a high-temperature ionic liquid pretreatment strategy for enzymatic hydrolysis of lignocellulosic feedstocks. FIG. 2B shows the same pretreatment process coupled with the method described herein, resulting in a low-temperature ionic liquid treatment process.

DETAILED DESCRIPTION OF THE INVENTION

Figure 1:
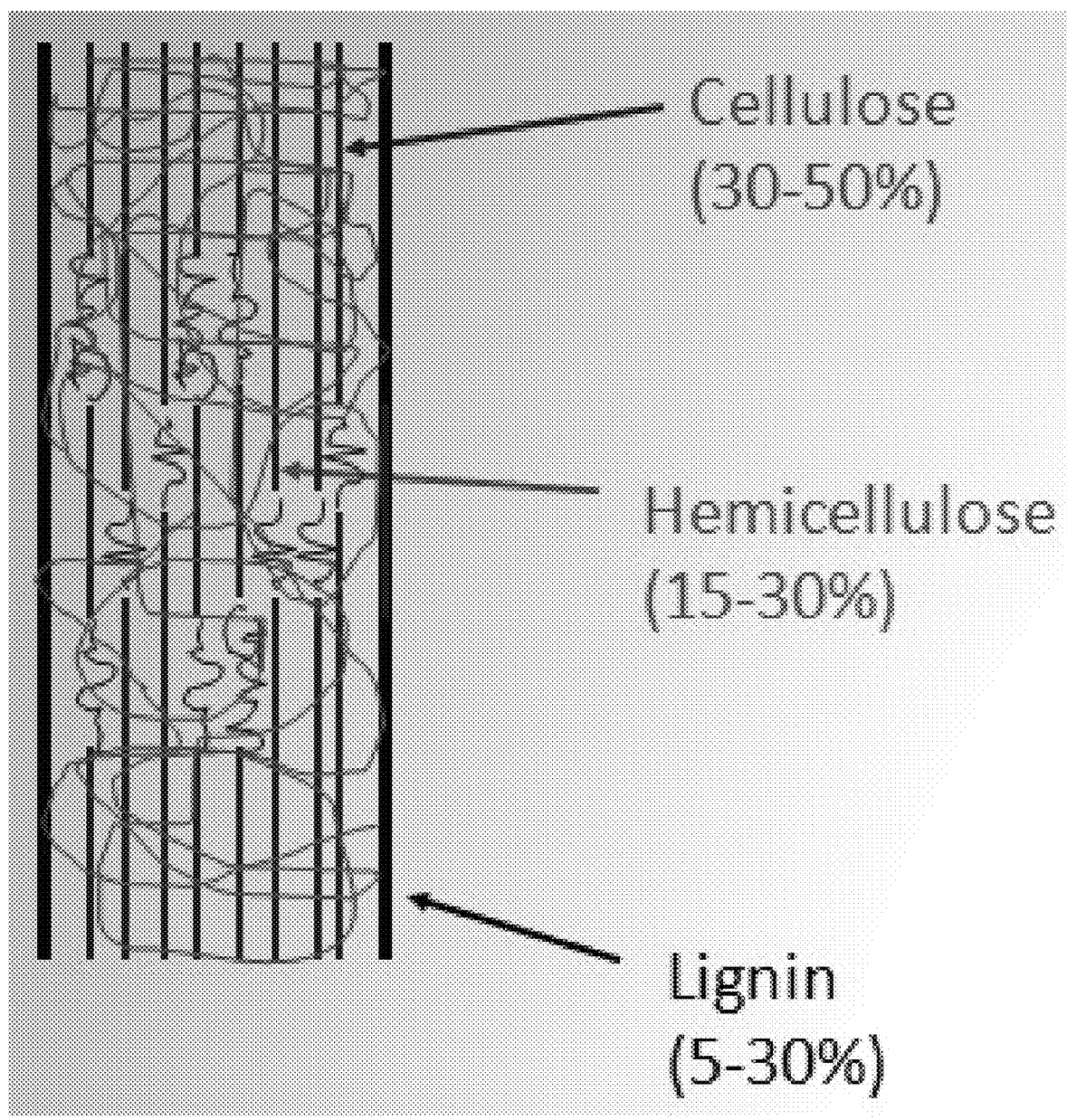
FIG. 1: Drawing of the structure of biomass containing cellulose, hemicellulose, and lignin. The cellulose, shown in blue, is a highly crystalline polymer of glucose or hexose, and a source of fermentable sugar. The hemicellulose, shown in green, is an amorphous polymer of xylose, hexose, and other fermentable sugars. The lignin, shown in black, is a cross-linked polymer network of phenyl propanoid subunits.

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this disclosure pertains.

Due to the structural complexity of lignocellulosic biomass, enzymatic inaccessibility to cellulose results in extremely slow enzymatic hydrolysis rates. One of the pathways to deconstruction of biomass to its constituent sugars is to utilize a pretreatment of substrates by chemical and/or thermal processes followed by enzymatic or acid-catalyzed hydrolysis. A number of these technologies have been developed to overcome the recalcitrance of this cellulosic carbon source to hydrolysis to its monomeric sugars. One such technology is ionic liquid (IL) incubation of biomass at various temperatures ranging between about 120° C. and about 160° C., which results in rapid and efficient enzyme hydrolysis. IL pretreatment produces amorphous cellulose that is accessible to water, catalysts, and enzymes, increasing the rate of hydrolysis of cellulose to glucose or soluble glucose oligomers and hemicellulose to its constituent sugars. However, with a one-step pretreatment of native lignocellulosic biomass consisting of ionic liquid incubation alone, high temperatures are often necessary to unravel the crystalline structure of cellulose. The native crystalline structure of cellulose is a major impediment to saccharification.

Provided herein is a method that reduces the energy input of IL incubation by lowering the ionic liquid incubation temperatures from 120-160° C. down to a range of from ambient temperatures to about 75° C. The method includes a low-temperature (such as room temperature) pre-processing step that precedes the ionic liquid incubation, where the pre-processing step involves lignin oxidation at ambient temperatures. This pre-processing step enables partial disruption of the biomass structure, and allows for low IL incubation temperatures with subsequently rapid saccharification as well as reduced biomass and ionic liquid degradation, contamination, and derivatization. The method can be used for any type of lignocellulosic biomass, including, but not limited to: poplar, switchgrass, rice straw, hardwood, softwood, herbaceous crops, recycled paper, waste paper, wood chips, pulp, paper wastes, waste wood, thinned wood, cornstalk, chaff, wheat straw, sugar cane stalk, bagasse, agricultural residual products, agricultural wastes, and combinations thereof.

Though IL incubation is specified in this description for illustrative purposes, the method of the present disclosure can be coupled with any suitable pretreatment step to produce advantageous results such as reduced required energy input and side reactions. Specifically, it is to be understood that the presently disclosed pre-processing step can be coupled with any of several non-IL pretreatment processes. Some non-limiting examples of other suitable pretreatment processes the pre-processing step can be coupled with include, but are not limited to: dilute acid hydrolysis, ammonia fiber explosion, pH-controlled liquid hot water treatment, aqueous ammonia recycling processes, and lime pretreatments. When the preprocessing step is coupled with an ionic liquid treatment step, the result is a dramatically lowered required temperature for the ionic liquid pretreatment step. Suitable ionic liquid pretreatment steps include, but are not limited to, those described in U.S. Pat. Nos. 7,674,608, 8,030,030, and 8,236,536, the entire disclosures of which are incorporated herein by reference. In certain embodiments, coupling a lignin oxidation step with ionic liquid pretreatment lowers the required ionic liquid pretreatment temperature by about 100° C.

Figure 2A:
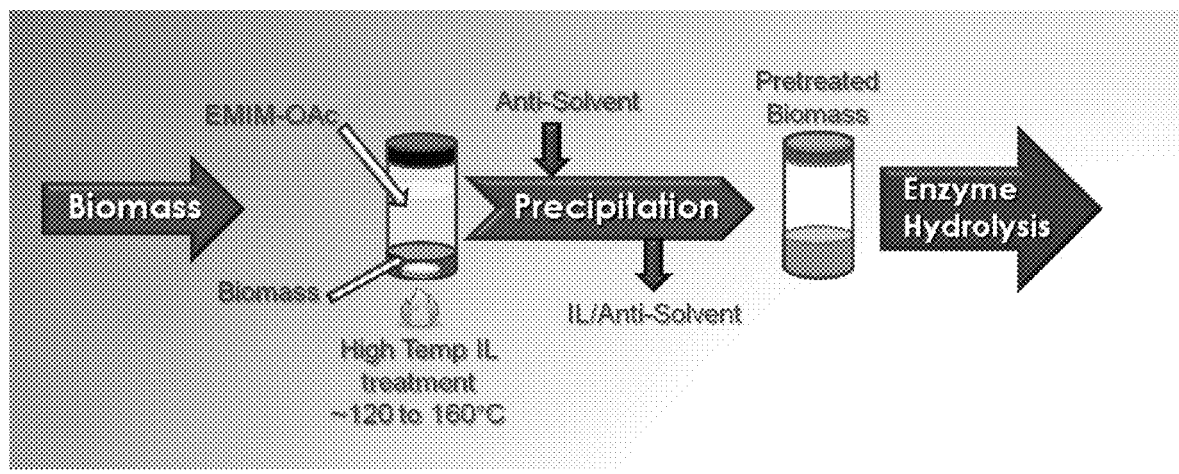
FIGS. 2A-B: Flow charts of exemplary ionic liquid pretreatment processes. EMIM-OAc is an example of an ionic liquid. The mixture of NaOH and $H_2O_2$ is an example of an alkaline oxidizing agent.
Figure 2B:
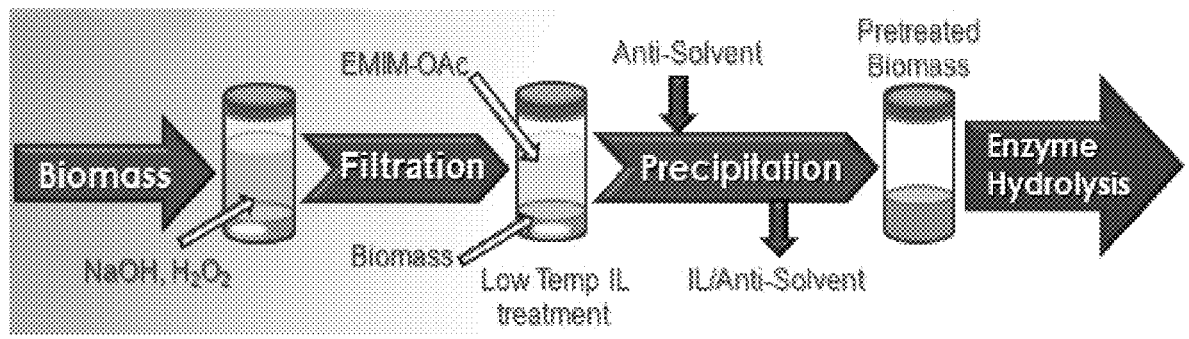
Figure 3A:
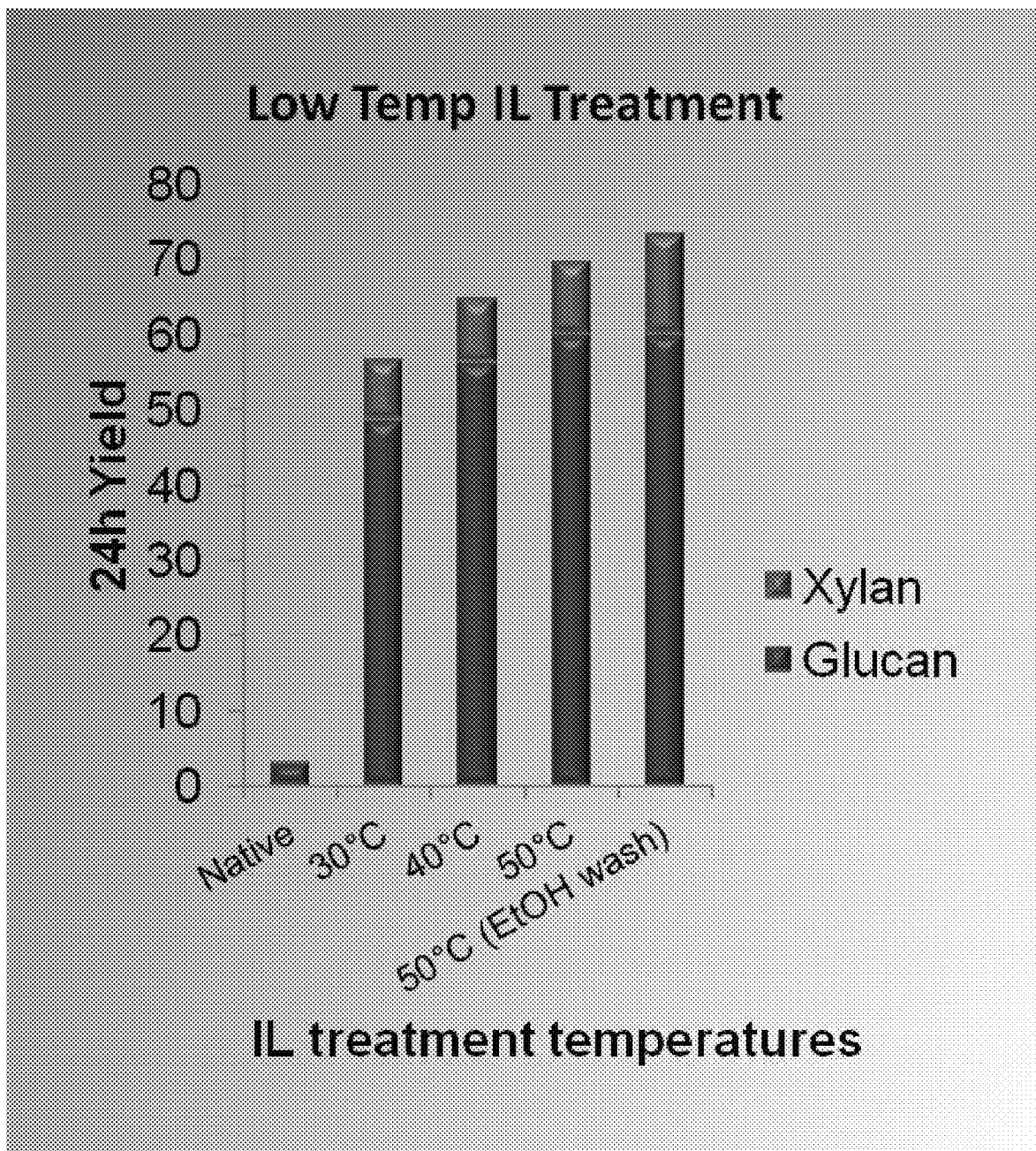
FIGS. 3A-B: Total sugar yield for poplar feedstock with a fixed enzyme loading per gram of glucan. These graphs illustrate the difference in yield resulting from methods involving a low temperature ionic liquid pretreatment step (FIG. 3A), as described herein, and (FIG. 3B) a high temperature ionic liquid treatment step.
Figure 3B:
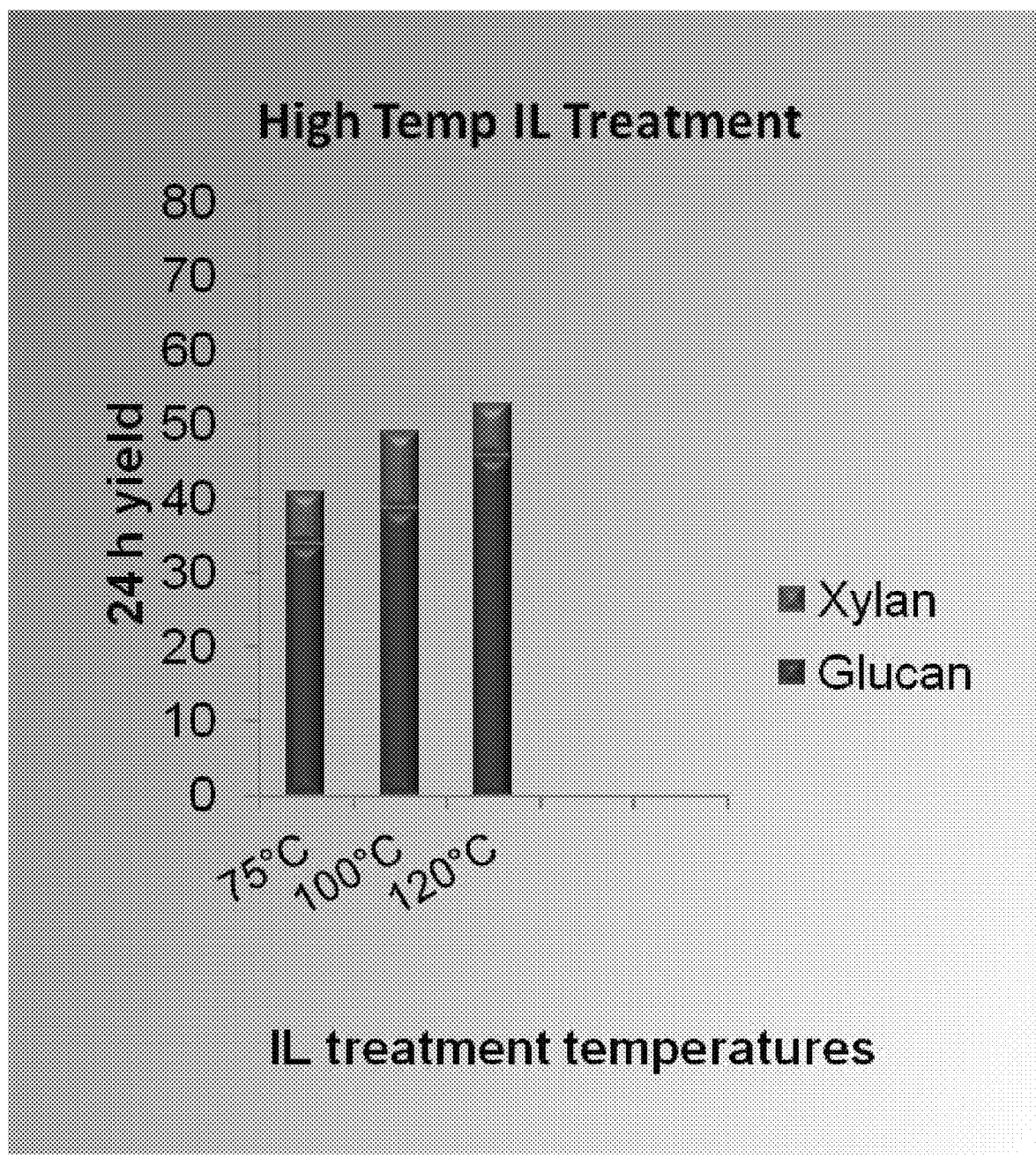
Figure 4A:
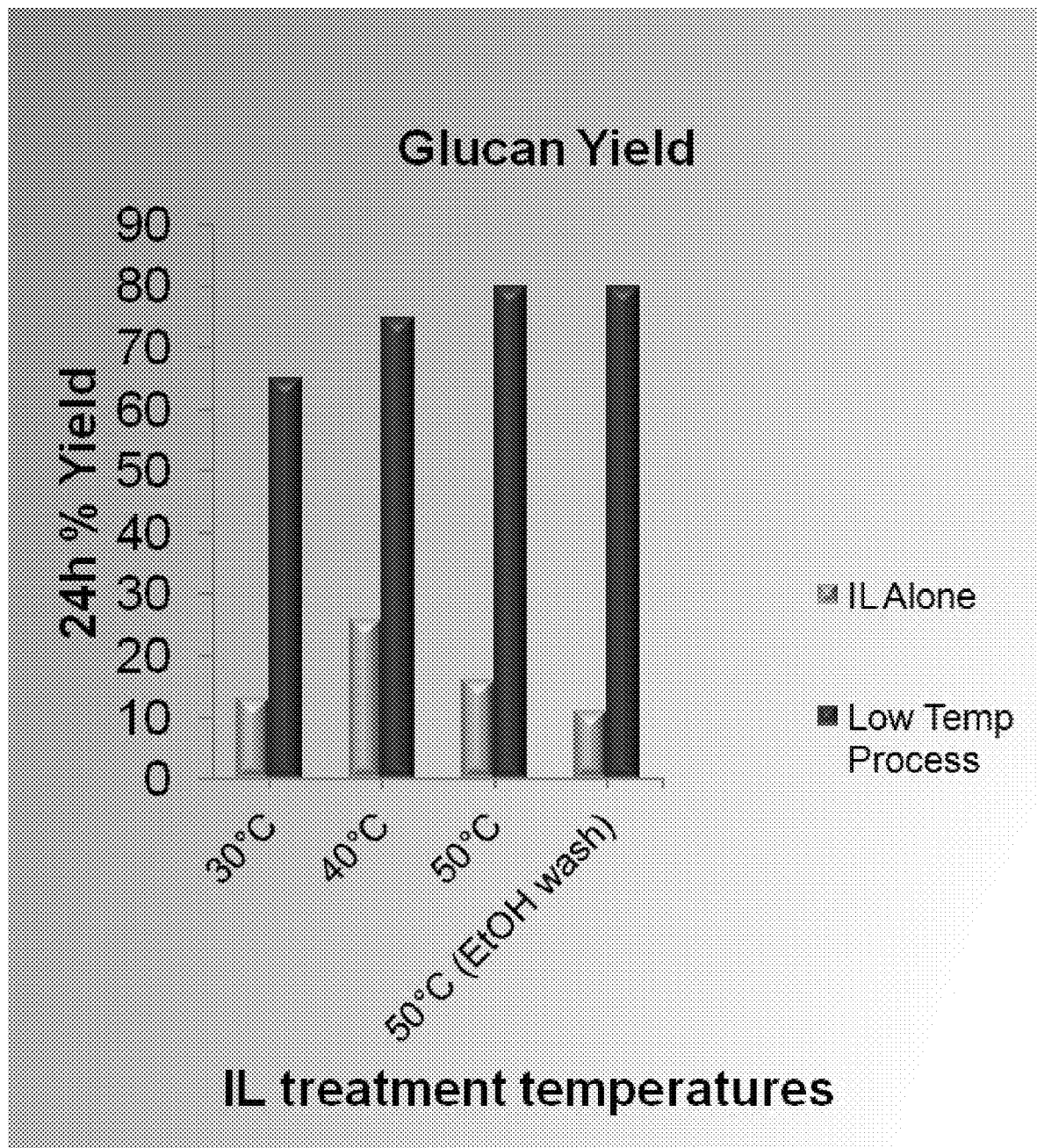
FIGS. 4A-B: Comparative yields of glucose (FIG. 4A) and xylose (FIG. 4B) for poplar feedstock, shown as a function of ionic liquid treatment temperature with a fixed enzyme loading per gram of feedstock using water as an anti-solvent unless otherwise noted.
Figure 4B:
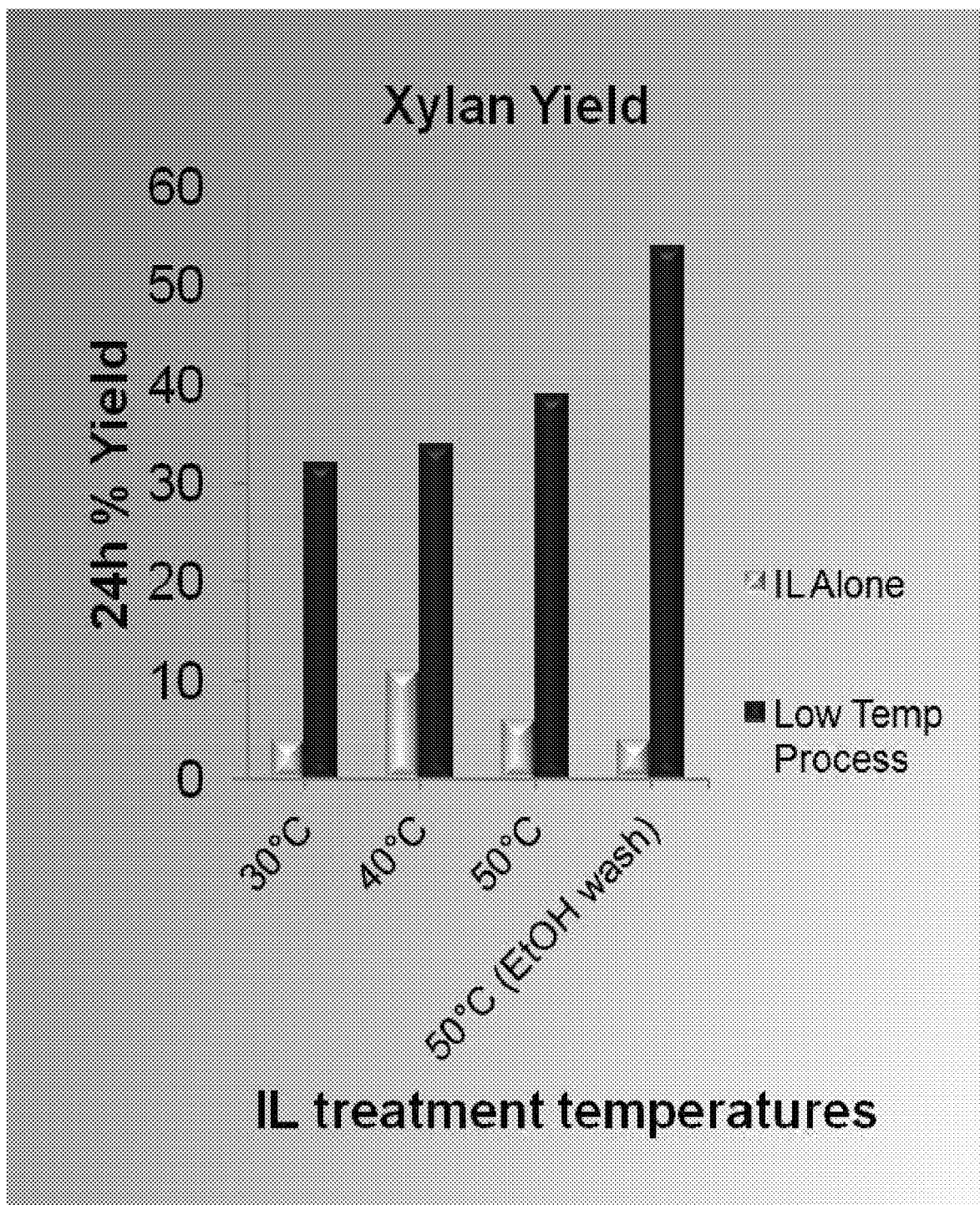

High-temperature ionic liquid pretreatment, ranging between about 120° C. and about 160° C., has previously been necessary to unravel the crystalline structure of cellulose in order to make it accessible to water and enzymes and thereby increase the rate of hydrolysis of cellulose to glucose or soluble glucose oligomers and hemicellulose to its constituent sugars such as xylose or soluble xylose oligomers. An example of an ionic liquid pretreatment is depicted in FIG. 2A. In the method described herein, a lignin oxidation step at ambient, or close to ambient, temperature and ambient pressure precedes the ionic liquid incubation (or other pretreatment step). This coupled pretreatment, a non-limiting example of which is depicted in FIG. 2B, enables partial deconstruction or redistribution of the lignin and the hemicellulose portions of lignocellulosic biomass, enables disruption of the crystalline structure of cellulose, and allows for the formation of dramatically more digestible amorphous cellulose and hemicellulose substrates without requiring high operation temperatures. Similar or higher digestibility yields can be gained at low IL incubation temperatures utilizing this method compared to that gained at elevated temperatures, as illustrated by FIGS. 3-4 and the examples described herein.

The method of the present disclosure involves conducting an oxidative pre-processing step prior to an IL incubation pretreatment. The oxidative pre-processing step is a lignin oxidation step, which can then be followed by low-temperature ionic liquid incubation. In certain embodiments, the oxidative pre-processing step significantly improves the efficiency of the yield and reaction rates of saccharification of lignocellulosic biomass while minimizing degradation or derivatization of biomass polysaccharides or IL.

In the lignin oxidation step, chemical delignification is achieved utilizing one or more suitable oxidizing agents. Suitable oxidizing agents include, but are not limited to: potassium peroxymonosulfate, ammonium persulfate, hydrogen peroxide (such as alkaline hydrogen peroxide solutions), calcium hypochlorite ($Ca(OCl)_2$), chlorine dioxide ($ClO_2$), ozone ($O_3$), t-butylhydroperoxide, dibenzoylperoxide, dimethyldioxirane, NaOCl, peracetic acid, trifluoroperacetic acid, perbenzoic acid, monoperoxyphthalic acid, metachlorobenzoic acid, 2-iodoxybenzoic acid, pyridine sulfur trioxide, bis(acetoxy)iodobenzene, bis(trifluoroacetoxy) iodobenzene, NaOBr, lead tetracetate, oxalyl chloride with dimethylsulfoxide (DMSO), nitric acid, nitrous oxide, sodium perborate (PBS), silver oxide, potassium nitrate, sulfuric acid, peroxymonosulfuric acid, osmium tetroxide, compounds having a hexavalent chromium atom, or a combination thereof.

The lignin oxidation step is conducted at ambient, or close to ambient, temperatures and pressure. In certain embodiments, the biomass is treated with the oxidizing agent(s) for a time period ranging from about 4 hours to about 48 hours. In one non-limiting example, the biomass is treated for about 6 hours. Once biomass is taken through the lignin oxidation step, the liquid phase is removed by filtration or other separation technique, and the solid is added directly to IL (or other pretreatment chemical) for incubation with or without drying. Prior washing is not necessary, though is possible.

The ionic liquid incubation typically lasts for a period of time of from about 1 hour to about 24 hours, and is typically at a temperature ranging from about 20° C. to about 75° C. In one non-limiting example, the temperature of the IL incubation is about 50° C. The optimal duration and temperature of the IL incubation step depend on the processing parameters of the lignin oxidation step, as well as the biomass source and feedstock properties such as composition, particle size, and moisture content. Washing steps after the lignin oxidation step and prior to IL treatment are not required, though may be included.

Any ionic liquid capable of swelling or dissolving cellulose or hemicellulose, such as those having a cation structure that includes imadazolium, pyrroldinium, pyridinium, phosphonium, or ammonium, can be used in combination with the lignin oxidation step of the present disclosure. Suitable ionic liquids for use in a coupled pretreatment method include, but are not limited to, ionic liquids represented by Formula I:

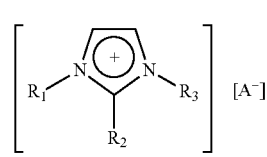

Formula I wherein each of $R_1$, $R_2$, and $R_3$ is hydrogen, an alkyl or alkoxy group having 1 to 8 carbon atoms, or an alkene group having 2 to 8 carbon atoms, wherein the alkyl group may be substituted with sulfone, sulfoxide, thioether, ether, amide, or amine; and A is a halide, acetate, formate, dicyanamide, carboxylate, phosphate, or other anion.

When the oxidative pre-processing step is coupled with ionic liquid pretreatment, the IL incubation results in partial or complete dissolution or swelling of the biomass. In certain embodiments, the IL incubation is then followed by rapid quenching with the addition of a cellulose and/or hemicellulose "anti-solvent" such as water, alcohol, acetonitrile, or other hydrophilic solvent in which the IL is soluble. The high affinity of anti-solvent for the IL leads to solute displacement of IL and recovery of a precipitated biomass (also referred to as regenerated biomass). The regenerated biomass is in an amorphous and solvent-swollen state. In solvent-swollen cellulose, the degree of crystallinity of the cellulose is progressively reduced as the extent of swelling increases. The regenerated biomass can be separated from the IL/anti-solvent solution through mechanical separations such as, but not limited to, centrifugation or filtration. In certain embodiments, the precipitated amorphous state is then taken through enzyme hydrolysis without drying. The saccharification can be performed with or without a catalyst. Suitable catalysts include, but are not limited to: $H_2SO_4$, HCl, HBr, $HNO_3$, $CH_3COOH$, HCOOH, $HClO_4$, $H_3PO_4$, paratoluene sulfonic acid (PTSA), or a mixture or complex thereof. The ionic liquid can also be recovered from the anti-solvent/IL mixture by flash distillation, solvent extraction, liquid-liquid extraction, membrane separation, or ion exchange techniques.

Disruption of cellulose, hemicellulose, and lignin linkages increases the accessibility of polysaccharides to water, catalysts, and/or enzymes, thereby increasing the rate of hydrolysis of cellulose to glucose or soluble glucose oligomers and hemicellulose to its constituent sugars. The lignin oxidation at ambient pressure and ambient, or close to ambient, temperature, preceding a low temperature ionic liquid incubation, causes partial deconstruction or redistribution of the lignin and hemicellulose portions of lignocellulosic biomass, enabling disruption of the crystalline structure of cellulose and the formation of dramatically more digestible amorphous cellulose and hemicellulose substrates without requiring high operation temperatures. This method is capable of achieving similar or higher digestibility yields in a two-step process with low IL incubation temperatures, compared to those achieved with a one-step IL incubation process at elevated temperatures.

Without wishing to be bound by theory, it is believed the improvement and efficiency of ionic liquid pretreatment at low temperatures resulting from the lignin oxidation pre-processing step is at least partly attributable to the oxidation of ferulate and other cross-links to hemicellulose, as well as the mild oxidation and solubilization of lignin. Alteration of linkages between monolignols and breakage in the lignin backbone lead to structural disruptions and smaller chain lengths. This results in lower hydrophobicity of the cell wall matrix and a lower glass transition temperature of lignin, which, in turn, allows for more efficient ionic liquid pretreatment at low temperatures.

The method of the present disclosure has many advantages. For example, the method increases the sustainability of lignocellulose processing, reduces energy input with low temperature IL incubation, increases the opportunity for effective heat integration and use of waste heat, increases the ease of recycling by reducing the hemicellulose fraction in IL/solvent, produces effective saccharification (hydrolysis to monomeric sugars) at very low enzyme loadings, and provides a renewable non-food-based source for sugar platform chemicals.

Figure 5:
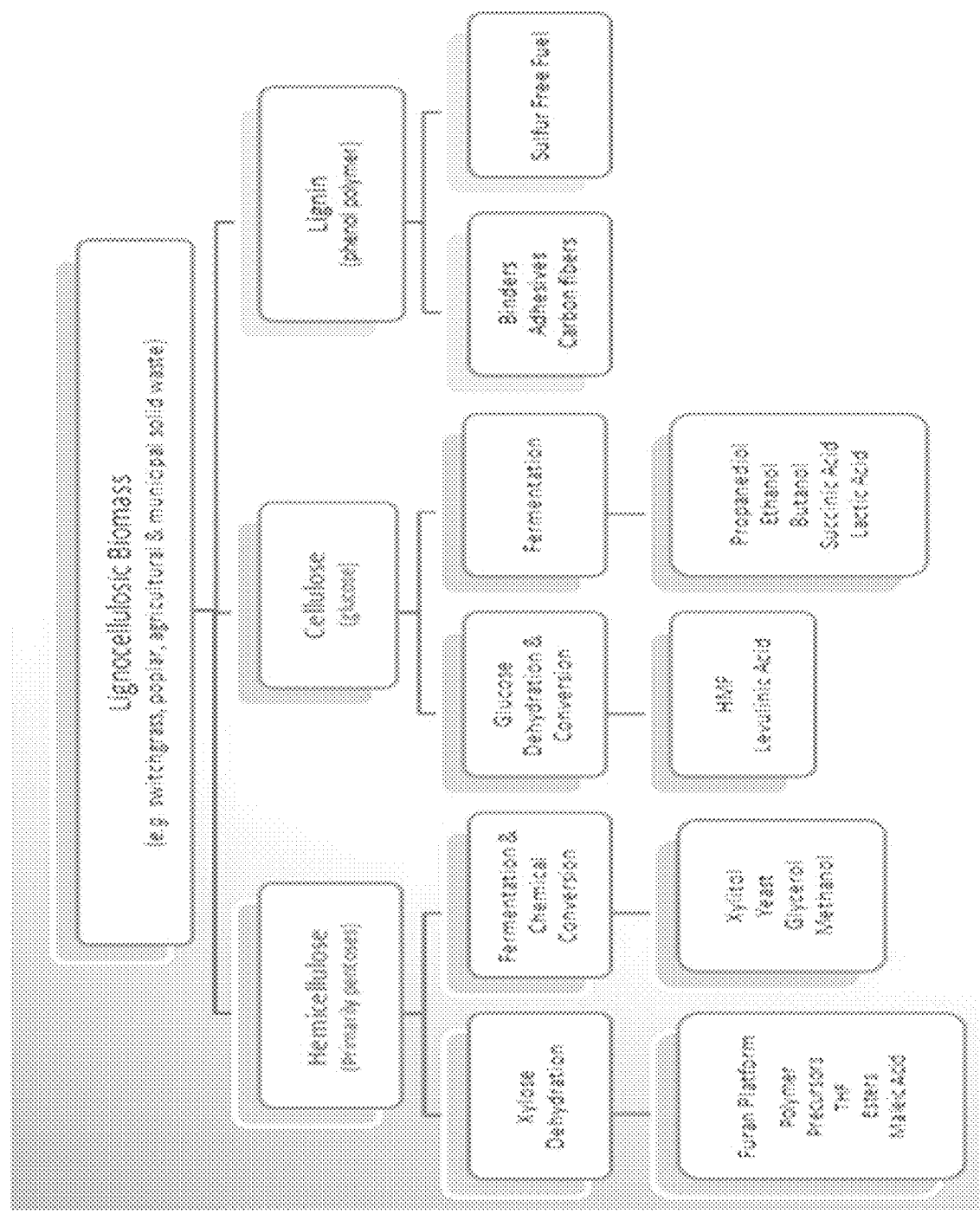
FIG. 5: Chart illustrating examples of possible sugar platform products.

The method of the present disclosure can be utilized to enhance saccharification of cellulose from biomass for fuel and chemical production, and is useful for producing a variety of valuable products from monomeric sugars. Possible products from the sugar platform include, but are not limited to: 1,3-propanediol, which is currently derived from corn grain (amylose) through glucose fermentation and is a green polymer precursor for the production of carpet, textiles, cosmetics, personal care products, and home care products; succinic acid, which is a polymer precursor for adhesives and coatings; and lactic acid, from the fermentation of glucose, which is a polymer precursor for packaging; PET precursors, such as polyethylene glycol from ethanol, which is a polymer precursor used in packaging; 1,4-butanediol (BDO); butylene glycol; furfural from xylose dehydration, which is used in resins, nylon, and as a platform for other classes of chemicals; and hydroxymethylfurfural (HMF), from glucose dehydration, which is used in lubricants and as a platform for the classes of chemicals. FIG. 5 shows a chart of some of the various sugar platform products that are possible from utilizing the hemicellulose, cellulose, and lignin of biomass.

Further described are methods to optimize the processing conditions for maximal sugar recovery and hydrolysis. For example, methods of minimizing the partitioning of xylan to IL/solvent to ease IL recovery are entirely within the scope of the present disclosure.

EXAMPLES

In the following examples, lignicellulosic biomass samples taken through both lignin oxidation and IL treatment steps with no drying prior to hydrolysis are referred to as "LOXIL-treated biomass". Samples taken through only IL treatment with no drying prior to hydrolysis are referred to as "IL-treated biomass."

An example of the preparation of LOXIL-treated biomass samples used in the following examples involves combining biomass with an oxidizing solution at 10% solids loading and incubating at room temperature from 4 hours to 24 hours with mixing using an orbital shaker water bath, a magnetic stirrer, or rollers. After lignin oxidation, liquid is removed from the solids through filtration. The solids are combined with 1-ethyl-3-methylimidazolium acetate (EMim-OAc) with a solids concentration of 5-20% in IL with or without drying prior to IL treatment. Samples are incubated at 20° C. to 75° C. for 1 hour to 24 hours with mixing. Anti-solvent is added to the IL incubation container and mixed vigorously, precipitating the biomass from EMim-OAc. The sample is briefly filtered or centrifuged and supernatant is removed. The solid is washed with solvent until the IL is displaced. After washing, the liquid is removed from the regenerated biomass solid through filtration.

An example of the preparation of the IL-treated biomass samples used in the following examples involves combining biomass with ionic liquid, 1-ethyl-3-methylimidazolium acetate (EMim-OAc), at 5 to 20% (w/w) solids loading and incubating at temperatures ranging from 20° C. to 75° C. for a time period of from 1 to 24 hours with mixing. Anti-solvent is added to the IL incubation container to precipitate the biomass from EMim-OAc, then mixed vigorously. The sample is filtered or centrifuged and the supernatant is removed. The solid is washed with solvent until the IL is displaced.

The terms "LOX," "LOX biomass," or "wet LOX" refer to biomass that is only taken through lignin oxidation at low temperatures ranging from room temperature to 40° C., from 4 hours to 24 hours. An example of the preparation of LOX biomass samples used in the following examples involves combining biomass with an oxidizing solution at 10% (w/w) solids loading and incubating at room temperature from 4 hours to 24 hours with mixing using an orbital shaker water bath, a magnetic stirrer, or rollers. All modes of mixing give similar results. After incubation, liquid is removed from the biomass solid through mechanical separation such as filtration.

Poplar, switchgrass, and corn stover were used as the biomass feedstocks in the examples below. However, many other types of biomass feedstocks can be used. The following Table 1 indicates the compositions of native biomass.

TABLE 1

Composition of native biomass analyzed with the National Renewable Energy Laboratory (NREL) protocol "Determination of Structural Carbohydrates and Lignin in Biomass" Crystallinity Index was estimated from X-ray powder diffraction data. Lignin includes both acid soluble and insoluble lignin.

| Substrate | Crystallinity Index (CrI) | Glucan (%) | Xylan (%) | Lignin (%) |
|---|---|---|---|---|
| Poplar | 36 | 47 ± 1 | 16 ± 0 | 26 ± 1 |
| Corn Stover | 33 | 34 | 18 | 15 |
| Switchgrass | 36 | 32 ± 0 | 19 ± 1 | 20 ± 1 |

Example 1

Structure of Pretreated Biomass

Figure 6A:
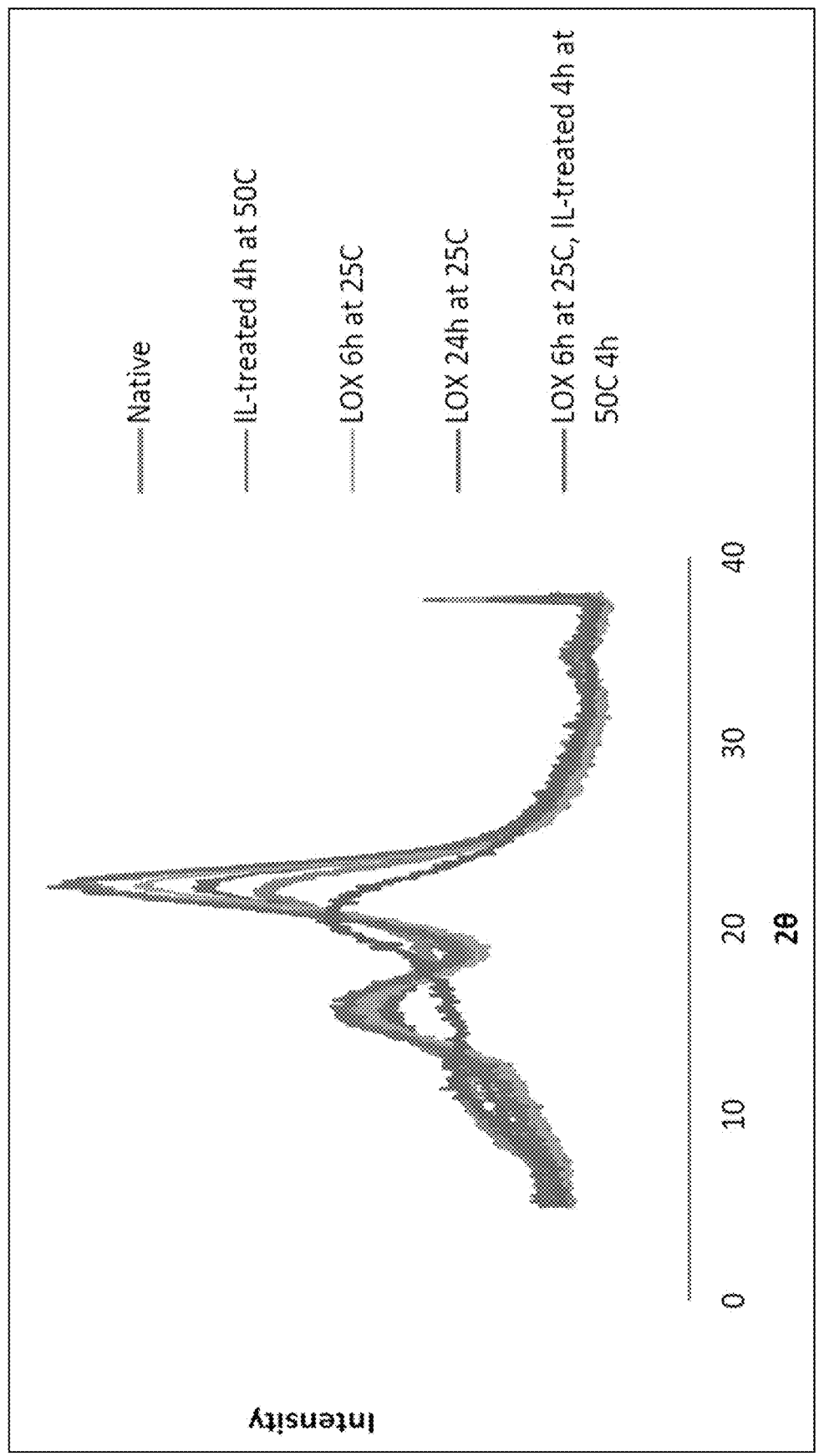
FIG. 6A: Comparative XRD intensity as a function of diffraction angle 2θ with a poplar substrate. LOX poplar was incubated in an alkaline hydrogen peroxide (AHP) mixture, as described in Example 2. Incubation times and temperatures are noted in the legand for the lignin oxidation and IL treatment steps.
Figure 6B:
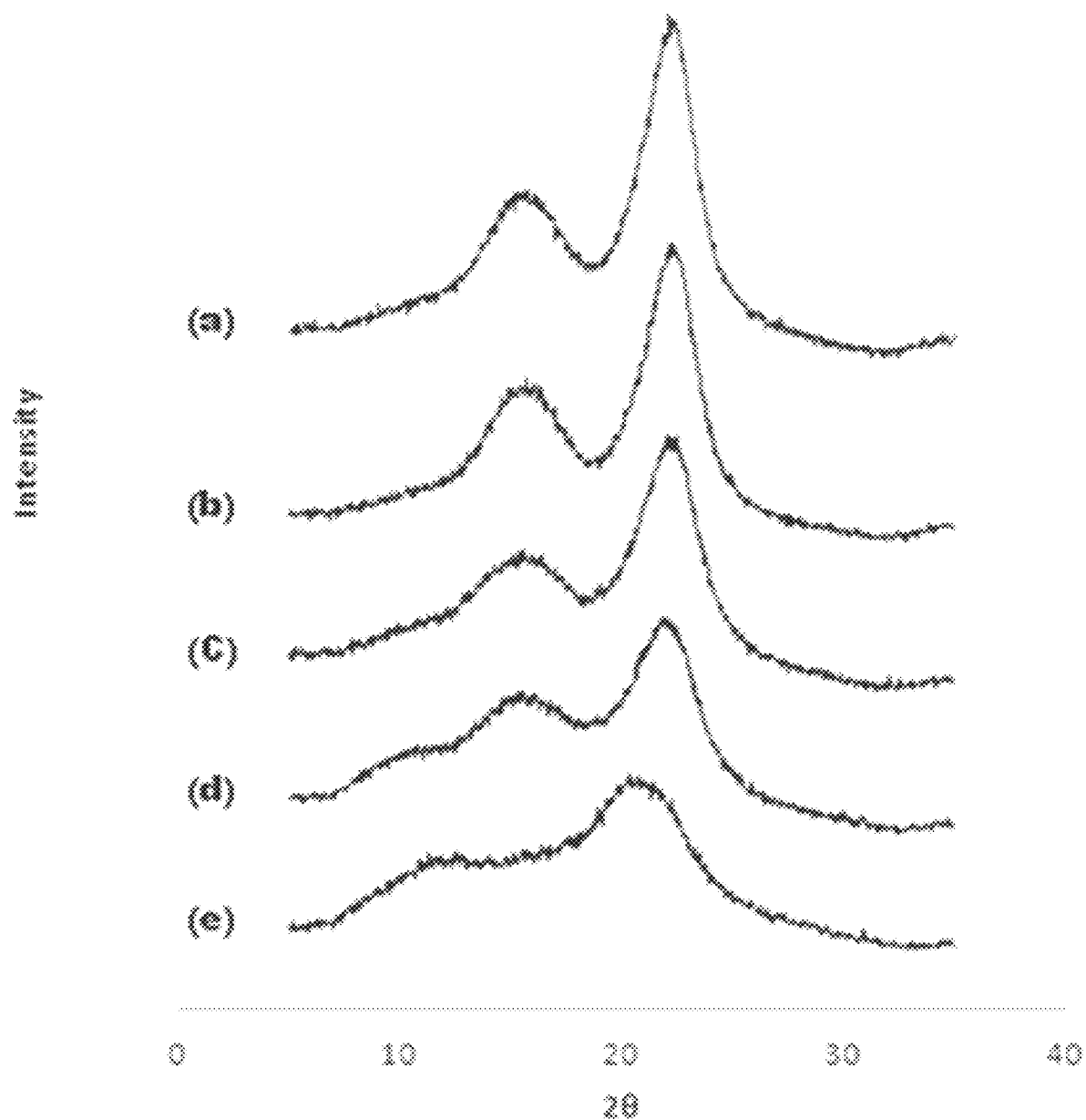
FIG. 6B: Same intensity plots as shown in FIG. 6B, depicted separately to better visualize each plot. (a) LOX 24 h at 25° C.; (b) LOX 6 h at 25° C.; (c) 4 h at 50° C. IL-treated; (d) native poplar; and (e) 6 h at 25° C. LOX followed by 4 h at 50° C. IL incubation.

X-ray powder diffraction (XRD) data were obtained to assess crystallinity for samples of LOX, LOXIL-treated, IL-treated, and native poplar. LOX, LOXIL-treated, and IL-treated poplar were dried under vacuum at 40° C. overnight. Samples were then ground using a mortar and pestle. Smooth films of powder for X-ray powder diffraction data collection were prepared. XRD data were collected at room temperature with a PANalytical XPERT' PRO powder diffractometer with an Xcelerator' detector using Nickel-filtered Cu-Kα radiation. Samples were scanned over the angular range 6.0-45.0° 2θ with a step size of 0.05°, and step time of 10 seconds. FIGS. 6A-6B show the comparative XRD intensity as a function of diffraction angle 2θ with a poplar substrate. LOX poplar was incubated in an alkaline hydrogen peroxide (AHP) mixture, described in Example 2 below. Diffraction data from bottom to top of FIG. 6B with incubation times and temperatures are: (a) LOX 24 h at 25° C.; (b) LOX 6 h at 25° C.; (c) 4 h at 50° C. IL-treated; (d) native poplar; and (e) 6 h at 25° C. LOX followed by 4 h at 50° C. IL incubation. (The baselines are offset for clarity.)

As seen in FIGS. 6A-6B, LOXIL-treated poplar produced amorphous cellulose whereas cellulose from IL-treated poplar, LOX poplar, and native poplar was highly crystalline. The XRD results indicate the two-step pretreatment process of room temperature lignin oxidation coupled with low temperature IL incubation disrupts cellulose crystallinity, whereas low temperature IL incubation alone or lignin oxidation alone increases the crystallinity of cellulose. This is further displayed in Table 2.

TABLE 2

Crystallinity index, CrI, of samples shown in FIGS. 6A-6B, estimated from the XRD data

| Poplar Substrates | CrI |
|---|---|
| Native | 36 |
| IL-treated (4 h at 5° C.) | 51 |
| LOX (6 h at 25° C.) | 58 |
| LOX (24 h at 25° C.) | 61 |
| LOX (6 h at 25° C.), IL-treated (4 h at 50° C.) | 10 |

Example 2

Enzyme Hydrolysis of Wet LOXIL-Treated Poplar with Lignin Oxidation at Room Temperature for 6 Hours, Using Alkaline Hydrogen Peroxide (AHP) Solution as the Oxidizing Solution, IL Treatment at 50° C. for 4 Hours and 5 wt % Loading, and Water as the Anti-Solvent Poplar was incubated for 6 hours in an oxidizing solution of a 10 wt % ratio of NaOH to biomass and a 12.5 wt % ratio of $H_2O_2$ to biomass. Water was added to a final concentration of 10% (w/v) biomass solids in the liquid solution. After lignin oxidation, the liquid was removed from the sample through mechanical means such as filtration, producing LOX poplar. The filtered LOX poplar was dried at 40° C. to constant weight. These solids were then combined with EMim-OAc at a 5 wt % biomass-to-ionic-liquid ratio for incubation for 4 hours at 50° C. The anti-solvent for this example was water. The anti-solvent-washed biomass was LOXIL-treated poplar.

Batch enzymatic hydrolysis of wet LOX, LOXIL-treated, IL-treated (4 hours at 50° C.), and native poplar was carried out in capped Erlenmeyer flasks immersed in an orbital shaker water bath at 50° C. for 24 hours. A commercial cellulase enzyme mixture, Cellic CTec2 (Novozyme), was used at an enzyme loading of 5.1 mg protein per gram of glucan, and a biomass concentration of about 1% (w/v). Native, IL-treated, LOX, and LOXIL-treated poplar were hydrolyzed using the same enzyme stock solution. Solutions were buffered with 0.05M sodium citrate, pH 4.8. Glucose and xylose concentrations in the hydrolysate were measured via high performance liquid chromatography (HPLC).

The average and standard deviation of replicate samples of 24-hour hydrolysis yields of glucose from glucan and xylose from xylan from treated and untreated poplar are shown in Table 3. Yields are reported as a percentage of monomeric sugars obtained from enzyme hydrolysis divided by the theoretical concentration of monomeric sugar based on the initial mass and composition of untreated biomass. Enzymatic hydrolysis glucose and xylose yields for LOXIL-treated poplar were 20 and 39 times greater than that of native poplar, respectively.

TABLE 3

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL and IL-treated poplar was water.

| Poplar Substrates | % Glucose Yield (Enhancement*) | % Xylose Yield (Enhancement*) |
|---|---|---|
| LOX (6 h at 25° C.), IL-treated (4 h at 50° C.) | 80 ± 2 (20) | 39 ± 3 (39) |
| IL-treated (4 h at 50° C.) | 16 ± 4 (4) | 6 ± 1 (6) |
| LOX (6 h at 25° C.) | 11 ± 0 (>2) | 1 ± 0 (1) |
| Native | 4 ± 0 | 1 ± 0 |

*Yield Enhancement is defined as the ratio of yield for treated biomass divided by that of untreated 'native' biomass.

Example 3

Enzyme Hydrolysis of Wet LOXIL-Treated Poplar with Lignin Oxidation at Room Temperature for 6 Hours, Using Alkaline Hydrogen Peroxide (AHP) Solution as the Oxidizing Solution, IL Treatment at 50° C. for 4 Hours and 5 wt % Solids Loading, and Ethanol as the Anti-Solvent Poplar was incubated at 25° C. for 6 hours in an oxidizing solution comprised of a 10 wt % ratio of NaOH to biomass and a 12.5 wt % ratio of $H_2O_2$ to biomass, as described in Example 2, to produce LOX poplar. For LOXIL-treated poplar, LOX samples were incubated in IL at 50° C. for 4 hours as described in Example 2. The anti-solvent ethanol was used to displace IL and to produce LOXIL-treated or IL-treated poplar. Batch enzymatic hydrolysis of wet LOX, LOXIL-treated, IL-treated, and native poplar was carried out as described in Example 2.

The average and standard deviation of replicate samples of the 24-hour hydrolysis yields are shown in Table 4 as a percentage of monomeric sugars obtained from enzyme hydrolysis divided by the theoretical concentration of monomeric sugar based on the initial mass and composition of untreated biomass. Glucose and xylose yields for LOXIL-treated poplar were at least 20 and 54 times greater than that of native poplar, respectively.

TABLE 4

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL-treated and IL-treated polar was ethanol.

| Poplar substrates | % Glucose Yield (Enhancement*) | % Xylose Yield (Enhancement*) |
|---|---|---|
| LOX (6 h at 25° C.), IL-treated (4 h at 50° C.) | 80 ± 0 (20) | 54 ± 2 (54) |
| IL-treated (4 h at 50° C.) | 11 ± 1 (>2) | 4 ± 1 (4) |
| LOX (6 h at 25° C.) | 11 ± 0 (>2) | 1 ± 0 (1) |
| Native | 4 ± 0 | 1 ± 0 |

*Yield Enhancement is defined as the ratio of yield for treated biomass divided by that of untreated native biomass.

Example 4

Enzyme Hydrolysis of Wet LOXIL-Treated Poplar with Lignin Oxidation at Room Temperature for 6 Hours, Using Alkaline Hydrogen Peroxide (AHP) Solution as the Oxidizing Solution, IL Treatment at 50° C. for 4 Hours and 15 wt % Solids Loading, and Water as the Anti-Solvent Poplar was incubated at 25° C. for 6 hours in an oxidizing solution comprised of a 10 wt % ratio of NaOH to biomass and a 12.5 wt % ratio of $H_2O_2$, as described in Example 2 except that the ratio of biomass to IL was increased to 15 wt % instead of 5 wt %. The anti-solvent water was used to displace IL and to produce LOXIL-treated or IL-treated poplar. Batch enzymatic hydrolysis of wet LOX, LOXIL-treated, IL-treated, and native poplar was carried out as described in Example 2.

The average and standard deviation of replicate samples of 24-hour hydrolysis yields of glucose from glucan and xylose from xylan from treated and untreated poplar are shown in Table 5. Yields are reported as a percentage of monomeric sugars obtained from enzyme hydrolysis divided by the theoretical concentration of monomeric sugar based on the initial mass and composition of untreated biomass. Glucose and xylose yields for LOXIL-treated poplar were 19 and 38 times greater than that of native poplar, respectively.

TABLE 5

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL and IL-treated poplar was water.

| Poplar Substrates | % Glucose Yield (Enhancement*) | % Xylose Yield (Enhancement*) |
|---|---|---|
| LOX (6 h at 25° C.), IL-treated (4 h at 50° C.) | 78$^d$ (19) | 38$^d$ (38) |
| IL-treated (4 h at 50° C.) | 16 ± 4 (4) | 6 ± 1 (6) |
| LOX (6 h at 25° C.) | 11 ± 0 (3) | 1 ± 0 (1) |
| Native | 4 ± 0 | 1 ± 0 |

*Yield Enhancement is defined as the ratio of yield for treated biomass divided by that of native biomass.
$^d$Average of duplicates

Example 5

Enzyme Hydrolysis of Wet LOXIL-Treated Corn Stover with Lignin Oxidation at Room Temperature for 24 Hours, Using Alkaline Hydrogen Peroxide (AHP) Solution as the Oxidizing Solution, IL Treatment at 50° C. for 4 Hours and 5 wt % Solids Loading, and Ethanol as the Anti-Solvent Corn stover was incubated at 25° C. for 24 hours in an oxidizing solution comprised of a 10 wt % ratio of NaOH to biomass and a 12.5 wt % ratio of $H_2O_2$ to biomass, as described in Example 2, to produce LOX corn stover. For LOXIL-treated corn stover, LOX samples were incubated in IL for 4 hours at 50° C., as described in Example 2. The anti-solvent ethanol was used to displace IL and to produce LOXIL-treated corn stover. Batch enzymatic hydrolysis of wet LOXIL-treated and native corn stover was carried out as described in Example 2.

The 24-hour hydrolysis yields of glucose from glucan and xylose from xylan from LOXIL-treated and untreated corn stover are shown in Table 6. Yields are reported as a percentage of monomeric sugars obtained from enzyme hydrolysis divided by the theoretical concentration of monomeric sugar based on the initial mass and composition of untreated biomass. Glucose and xylose yields for LOXIL-treated corn stover were at least 3 and 7 times greater than that of native corn stover, respectively.

TABLE 6

Twenty-four hour enzymatic hydrolysis yields of monomeric sugars for treated and native corn stover substrates. 10 mg/ml of treated or native corn stover samples were hydrolyzed at an enzyme loading of 5.1 mg protein per gram of glucan. Anti-solvent for LOXIL corn stover was ethanol.

| Corn Stover Substrates | % Glucose Yield (Enhancement*) | % Xylose Yield (Enhancement*) |
|---|---|---|
| LOX (24 h at 25° C.), IL-treated (4 h at 50° C.) | 72.5$^d$ (>3) | 51.5$^d$ (>7) |
| IL-treated (4 h at 50° C.) | 31 ± 0 | 17 ± 1 |
| LOX (24 h at 25° C.) | 40 ± 0 (>3) | 35 ± 1 (5) |
| Native | 24$^d$ | 7$^d$ |

*Yield Enhancement is defined as the ratio of yield for treated biomass divided by that of untreated biomass.
$^d$Average of duplicates

Example 6

Enzyme Hydrolysis of Wet LOXIL-Treated Switchgrass with Lignin Oxidation at Room Temperature for 24 Hours, Using AHP Solution as the Oxidizing Solution, IL Treatment at 50° C. for 4 Hours with 5 wt % Solids Loading, and Ethanol as the Anti-Solvent Switchgrass was incubated at 25° C. for 24 hours in an oxidizing solution comprised of a 10 wt % ratio of NaOH to biomass and a 12.5 wt % ratio of $H_2O_2$ to biomass, as described in Example 2, to produce LOX switchgrass. For LOXIL-treated switchgrass, LOX samples were incubated in IL for 4 hours at 50° C. with 5 wt % biomass loading in IL, as described in Example 2. The anti-solvent ethanol was used to displace IL and to produce LOXIL-treated switchgrass. Batch enzymatic hydrolysis of wet LOXIL-treated, IL-treated, and native switchgrass was carried out as described in Example 2.

The 24-hour hydrolysis yields of glucose from glucan and xylose from xylan from treated and untreated switchgrass are shown in Table 7. Yields are reported as a percentage of monomeric sugars obtained from enzyme hydrolysis divided by the theoretical concentration of monomeric sugar based on the initial mass and composition of untreated biomass. Glucose and xylose yields for LOXIL-treated switchgrass were approximately 5 and 16 times greater than that of native switchgrass, respectively.

TABLE 7

Twenty-four hour enzymatic hydrolysis yields of monomeric sugars for treated and native switchgrass substrates. 10 mg/ml of treated or native switchgrass samples were hydrolyzed at an enzyme loading of 5.1 mg protein per gram of glucan. Anti-solvent for LOXIL-treated and IL-treated switchgrass was ethanol.

| Switchgrass Substrates | % Glucose Yield (Enhancement*) | % Xylose Yield (Enhancement*) |
|---|---|---|
| LOX (24 h at 25° C.), IL-treated (4 h at 50° C.) | 54$^d$ (>4) | 32$^d$ (16) |
| IL-treated (4 h at 50° C.) | 15 ± 1 | 4 ± 0 |
| LOX (24 h at 25° C.) | 29 ± 0 | 19 ± 0 |
| Native | 12$^d$ | 2$^d$ |

*Yield Enhancement is defined as the ratio of yield for treated biomass divided by that of untreated native biomass.
$^d$Average of duplicates Example 7

Enzyme Hydrolysis of Wet LOXIL-Treated Poplar with Lignin Oxidation at Room Temperature for 24 Hours, Using AHP Solution as the Oxidizing Solution, IL Treatment at 40° C. for 24 Hours with 5 wt % Solids, and Water as the Anti-Solvent Poplar was incubated at 25° C. for 24 hours in an oxidizing solution comprised of a 10 wt % ratio of NaOH to biomass and a 12.5 wt % ratio of $H_2O_2$ to biomass, as described in Example 2, to produce LOX poplar. For LOXIL-treated poplar, LOX samples were incubated in IL at 40° C. for 24 hours with 5 wt % biomass loading in IL, as described in Example 2. The anti-solvent water was used to displace IL and to produce LOXIL-treated poplar. Batch enzymatic hydrolysis of wet LOXIL-treated, IL-treated, and native poplar was carried out as described in Example 2.

The 24-hour hydrolysis yields of glucose from glucan and xylose from xylan for treated and untreated poplar are shown in Table 8. Yields are reported as a percentage of monomeric sugars obtained from enzyme hydrolysis divided by the theoretical concentration of monomeric sugar based on the initial mass and composition of untreated biomass. Glucose and xylose yields for LOXIL-treated poplar were at least 18 and 32 times greater than that of native poplar, respectively.

TABLE 8

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL-treated and IL-treated poplar was water.

| Poplar Substrates | % Glucose Yield (Enhancement*) | % Xylose Yield (Enhancement*) |
|---|---|---|
| LOX (24 h at 25° C.) IL-treated (24 h at 40° C.) | 74 ± 2 (>18) | 32 ± 2 (32) |
| IL-treated (24 h at 40° C.) | 24$^d$ (>6) | 11$^d$ (13) |
| LOX (24 h at 25° C.) | 13 ± 0 (>3) | 19 ± 1 (19) |
| Native | 4 ± 0 | 1 ± 0 |

*Yield Enhancement is defined as the ratio of yield for treated biomass divided by that of untreated native biomass.
$^d$Average of duplicates Example 8

Enzyme Hydrolysis of Wet LOXIL-Treated Poplar with Lignin Oxidation at Room Temperature for 24 Hours, Using AHP Solution as the Oxidizing Solution, IL Treatment at 30° C. for 24 Hours with 5 wt % Solids Loading, and Water as the Anti-Solvent Poplar was incubated at 25° C. for 24 hours in an oxidizing solution comprised of a 10 wt % ratio of NaOH to biomass and a 12.5 wt % ratio of $H_2O_2$ to biomass, as described in Example 2, to produce LOX poplar. For LOXIL-treated poplar, LOX samples were incubated in IL at 30° C. for 24 hours with 5 wt % biomass loading in IL, as described in Example 2. The anti-solvent water was used to displace IL and to produce LOXIL-treated poplar. Batch enzymatic hydrolysis of wet LOXIL-treated, wet IL-treated, and native poplar was carried out as described in Example 2.

The 24-hour hydrolysis yields of glucose from glucan and xylose from xylan for treated and untreated poplar are shown in Table 9. Yields are reported as a percentage of monomeric sugars obtained from enzyme hydrolysis divided by the theoretical concentration of monomeric sugar based on the initial mass and composition of untreated biomass. Glucose and xylose yields for LOXIL-treated poplar were at least 16 and 32 times greater than that of native poplar, respectively.

TABLE 9

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL and IL-treated poplar was water.

| Poplar Substrates | % Glucose Yield (Enhancement*) | % Xylose Yield (Enhancement*) |
|---|---|---|
| LOX (24 h at 25° C.), IL-treated (24h at 30° C.) | 65 ± 2 (>16) | 32 ± 2 (32) |
| IL-treated (24 h at 30° C.) | 13$^d$ (>3) | 4$^d$ (4) |
| LOX (24 h at 25° C.) | 13 ± 0 (>3) | 19 ± 1 (19) |
| Native | 4 ± 0 | 1 ± 0 |

*Yield Enhancement is defined as the ratio of yield for treated biomass divided by that of untreated biomass.
$^d$Average of duplicates Example 9

Enzyme Hydrolysis of LOXIL-Treated Poplar with Lignin Oxidation for 24 Hours, Using Potassium Peroxymonosulfate Triple Salt Solution as the Oxidizing Solution, IL Treatment at 75° C. for 4 Hours and 5 wt % Solids Loading, and Water as the Anti-Solvent Poplar was incubated for 24 hours in an oxidizing solution comprised of 65 mM potassium peroxymonosulfate triple salt ($2KHSO_5 \cdot KHSO_4 \cdot K_2SO_4$, average molecular weight of 614.76 g/mol) in water. Water was added such that a 10% (w/v) biomass-to-liquid solution was obtained. After lignin oxidation, the liquid was removed from the poplar via filtration, producing LOX poplar. The LOX poplar was not further dried after filtration. For LOXIL-treated poplar, LOX samples were incubated in IL at 75° C. for 4 hours with 5 wt % biomass loading in IL, as described in Example 2. The anti-solvent water was used to displace IL and to produce LOXIL-treated poplar. Batch enzymatic hydrolysis of wet LOXIL-treated, IL-treated, and native poplar was carried out as described in Example 2.

The 24-hour hydrolysis yields of glucose from glucan and xylose from xylan for treated and untreated poplar are shown in Table 10. Yields are reported as a percentage of monomeric sugars obtained from enzyme hydrolysis divided by the theoretical concentration of monomeric sugars obtained from enzyme hydrolysis divided by the theoretical concentration of monomeric sugar based on the initial mass and composition of untreated biomass. Glucose and xylose yields for LOXIL-treated poplar were 18 and 52 times greater than that of native poplar, respectively.

TABLE 10

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL-treated and IL-treated poplar was water.

| Poplar Substrates | % Glucose Yield (Enhancement*) | % Xylose Yield (Enhancement*) |
|---|---|---|
| LOX (24 h at 40° C.), IL-treated (4 h at 75° C.) | 72 ± 2 (18) | 52 ± 5 (52) |
| IL-treated (4 h at 75° C.) | 45 ± 2 (>11) | 29 ± 4 (29) |
| LOX (24 h at 40° C.) | $4^s$ (4) | $2^s$ (2) |
| Native | 4 ± 0 | 1 ± 0 |

*Yield Enhancement is defined as the ratio of yield for treated biomass divided by that of untreated biomass.
$^d$Average of duplicates
$^s$Single measurement Example 10

Enzyme Hydrolysis of LOXIL-Treated Poplar with Lignin Oxidation at 40° C. for 24 Hours, Using Ammonium Persulfate as the Oxidizing Solution, IL Treatment at 75° C. for 4 Hours and 5 wt % Solids Loading, and Water as the Anti-Solvent Poplar was incubated at 40° C. for 24 hours in an oxidizing solution comprised of 0.34M ammonium persulfate, $(NH_4)_2S_2O_8$, in water. Water was added such that a 10% (w/v) biomass-to-liquid solution was obtained. After lignin oxidation, the liquid was removed via filtration, producing LOX poplar. The LOX poplar was not further dried after filtration. For LOXIL-treated poplar, LOX samples were incubated in IL at 75° C. for 4 hours with 5 wt % biomass loading in IL, as described in Example 2. The anti-solvent water was used to displace IL and to produce LOXIL-treated poplar. Batch enzymatic hydrolysis was wet LOXIL-treated, IL-treated, and native poplar was carried out as described in Example 2.

The 24-hour hydrolysis yields of glucose from glucan and xylose from xylan for treated and untreated poplar are shown in Table 11. Yields are reported as a percentage of monomeric sugars obtained from enzyme hydrolysis divided by the theoretical concentration of monomeric sugar based on the initial mass and composition of untreated biomass. Glucose and xylose yields for LOXIL-treated poplar were 15 and 46 times greater than that of native poplar, respectively.

TABLE 11

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL-treated and IL-treated poplar was water.

| Poplar substrates | % Glucose Yield (Enhancement*) | % Xylose Yield (Enhancement*) |
|---|---|---|
| LOX (24 h at 40° C.), IL-treated (4 h at 75° C.) | $60^s$ (15) | $46^s$ (46) |
| IL-treated (4 h at 75° C.) | 45 ± 2 (>11) | 29 ± 4 (29) |
| LOX (24 h at 40° C.) | $4^s$ (4) | $2^s$ (2) |
| Native | 4 ± 0 | 1 ± 0 |

*Yield Enhancement is defined as the ratio of yield for treated biomass divided by that of untreated biomass.
$^d$Average of duplicates
$^s$Singlet Example 11

Enzyme Hydrolysis of LOXIL-Treated Poplar with Lignin Oxidation at 25° C. for 6 Hours, Using AHP as the Oxidizing Solution, IL Treatment at 40° C. for 24 Hours and 5 wt % Solids Loading, and Water as the Anti-Solvent Poplar was incubated at 25° C. for 6 hours in an alkaline solution comprised of a 10 wt % ratio of NaOH to biomass and a 12.5 wt % ratio of $H_2O_2$ to biomass, as described in Example 2, to produce LOX poplar. For LOXIL-treated poplar, LOX samples were incubated in IL at 40° C. for 24 hours with 5 wt % biomass loading in IL, as described in Example 2. The anti-solvent water was used to displace IL and to produce LOXIL-treated poplar. Batch enzymatic hydrolysis of wet LOXIL-treated, wet IL-treated, and native poplar was carried out as described in Example 2.

The 24-hour hydrolysis yields of glucose from glucan and xylose from xylan for treated and untreated poplar are shown in Table 12. Yields are reported as a percentage of monomeric sugars obtained from enzyme hydrolysis divided by the theoretical concentration of monomeric sugar based on the initial mass and composition of untreated biomass. Enzymatic hydrolysis glucose and xylose yields for LOXIL-treated poplar were 18 and 34 times greater than that of native poplar, respectively.

TABLE 12

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL and IL-treated poplar was water.

| Poplar Substrates | % Glucose Yield (Enhancement*) | % Xylose Yield (Enhancement*) |
|---|---|---|
| LOX (6 h at 25° C.), IL-treated (24 h at 40° C.) | $75^d$ (>18) | 34 (34) |
| IL-treated (24 h at 40° C.) | $24^d$ (6) | $11^d$ (11) |
| LOX (6 h at 25° C.) | 11 ± 0 (>2) | 1 ± 0 (1) |
| Native | 4 ± 0 | 1 ± 0 |

*Yield Enhancement is defined as the ratio of yield for treated biomass divided by that of untreated biomass.
$^d$Average of duplicates

Example 12

Enzyme Hydrolysis of Wet LOXIL-Treated Poplar with Lignin Oxidation at Room Temperature for 6 Hours, Using AHP Solution as the Oxidizing Solution, IL Treatment at 30° C. for 24 Hours with 5 wt % Solids Loading, and Water as the Anti-Solvent Poplar was incubated for 6 hours in an oxidizing solution comprised of a 10 wt % ratio of NaOH to biomass and a 12.5 wt % ratio of $H_2O_2$ to biomass, as described in Example 2, to produce LOX poplar. For LOXIL-treated poplar, LOX samples were incubated in IL at 30° C. for 24 hours with 5 wt % biomass loading in IL, as described in Example 2. The anti-solvent water was used to displace IL and to produce LOXIL-treated poplar. Batch enzymatic hydrolysis of wet LOXIL-treated, wet IL-treated, and native poplar was carried out as described in Example 2.

The 24-hour hydrolysis yields of glucose from glucan and xylose from xylan for treated and untreated poplar are shown in Table 13. Yields are reported as a percentage of monomeric sugars obtained from enzyme hydrolysis divided by the theoretical concentration of monomeric sugar based on the initial mass and composition of untreated biomass. Enzymatic hydrolysis glucose and xylose yields for LOXIL-treated poplar were 16 and 31 times greater than that of native poplar, respectively.

TABLE 13

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL-treated and IL-treated poplar was water.

| Poplar Substrates | % Glucose Yield (Enhancement*) | % Xylose Yield (Enhancement*) |
|---|---|---|
| LOX (6 h at 25° C.), IL-treated (24 h at 30° C.) | $66^d$ (>16) | 31 (31) |
| IL-treated (24 h at 30° C.) | $13^d$ (6) | $4^d$ (11) |
| LOX (6 h at 25° C.) | 11 ± 0 (>2) | 1 ± 0 (1) |
| Native | 4 ± 0 | 1 ± 0 |

*Yield Enhancement is defined as the ratio of yield for treated biomass divided by that of untreated biomass.
$^d$Average of duplicates

Example 13

Enzyme Hydrolysis of Wet LOXIL-Treated Poplar with Lignin Oxidation at Room Temperature for 6 Hours, Using AHP Solution as the Oxidizing Solution, Wet IL Treatment at 75° C. for 4 Hours and 5 wt % Loading, and Water as the Anti-Solvent Poplar was incubated for 6 hours in an oxidizing solution of a 10 wt % ratio of NaOH to biomass and a 12.5 wt % ratio of $H_2O_2$ to biomass. Water was added to a final concentration of 10% (w/v) biomass solids in the liquid solution. After lignin oxidation, the liquid was removed from the sample through mechanical means such as filtration, producing wet LOX poplar. Without further drying, wet LOX poplar was then combined with EMim-OAc at a 5 wt % biomass-to-ionic-liquid ratio (based on dry weight) for incubation for 4 hours at 50° C. The anti-solvent for this example was water. Batch enzymatic hydrolysis of wet LOXIL-treated, wet IL-treated, and native poplar was carried out as described in Example 2.

The average and standard deviation of replicate samples of 24-hour hydrolysis yields of glucose from glucan and xylose from xylan from treated and untreated poplar are shown in Table 14. Yields are reported as a percentage of monomeric sugars obtained from enzyme hydrolysis divided by the theoretical concentration of monomeric sugar based on the initial mass and composition of untreated biomass. Enzymatic hydrolysis glucose and xylose yields for LOXIL-treated poplar were at least 18 and 52 times greater than that of native poplar, respectively.

TABLE 14

Twenty-four hour enzymatic hydrolysis yields of monomeric sugars for treated and native poplar substrates. 10 mg/ml of treated or native poplar samples were hydrolyzed at an enzyme loading of 5.1 mg protein per gram of glucan. Anti-solvent for LOXIL and IL-treated poplar was water.

| Poplar Substrates | % Glucose Yield (Enhancement*) | % Xylose Yield (Enhancement*) |
|---|---|---|
| LOX (6 h at 25° C.), IL-treated (4 h at 75° C.) | 75 ± 1 (>18) | 52 ± 5 (52) |
| IL-treated (4 h at 75° C.) | 45 ± 2 (>11) | 29 ± 4 (29) |
| LOX (6 h at 25° C.) | 11 ± 0 (>2) | 1 ± 0 (1) |
| Native | 4 ± 0 | 1 ± 0 |

Certain embodiments of the methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A low temperature method of treating a non-fermented lignocellulosic biomass for production of a non-fermented amorphous lignocellulosic product, the lignocellulosic biomass having a lignin component, a hemicellulose component, and a cellulose component, the method comprising:
    in a first step, contacting the non-fermented lignocellulosic biomass with an oxidizing agent at a first temperature ranging from 18° C. to 40° C. for a first period of time sufficient to at least partially decompose the lignin component and to cause disruption of cellulose, hemicellulose, and lignin linkages in the lignocellulose biomass, while minimizing degradation or derivatization of the hemicellulose component and the cellulose component, thereby producing a non-fermented lignin oxidized (LOX) biomass;
    thereafter, in a second step, contacting the non-fermented LOX biomass of the first step with an ionic liquid (IL) at a second temperature of 25° C. to 40° C. for a second period of time, thereby producing a first mixture comprising an IL and LOX biomass;
    thereafter, in a third step, contacting the first mixture of the third step with a solvent, thereby producing a second mixture comprising a non-fermented LOXIL-treated (lignin oxidized and IL incubated) biomass and solvent, wherein the IL is soluble in the solvent and at least one of the cellulose or the hemicellulose components of the second mixture is insoluble in the solvent; and, in a fourth step, separating the LOXIL-treated biomass from the solvent to produce the non-fermented amorphous lignocellulosic product;

wherein the method produces a glucose yield of from 63% to 76% and a xylose yield of from 31% to 34%.

2. The method of claim 1, wherein the non-fermented lignocellulosic biomass comprises poplar, corn stover, switchgrass, or a combination thereof.

3. The method of claim 1, wherein the separating comprises mixing the second mixture so as to precipitate the non-fermented LOXIL-treated biomass from the IL.

4. The method of claim 3, further comprising washing the precipitated non-fermented LOXIL-treated biomass with the solvent so as to displace the IL.

5. The method of claim 3, further comprising removing liquid from the precipitated non-fermented LOXIL-treated biomass through filtration.

6. The method of claim 1, further comprising the step of contacting the second mixture with an acid catalyst to hydrolyze at least one of the hemicellulose component or the cellulose component.

7. The method of claim 1, further comprising the step of contacting the non-fermented lignocellulosic biomass with enzymes capable of hydrolyzing at least one of the cellulose component or the hemicellulose component, and converting at least one of the cellulose component or the hemicellulose component to hexose and/or pentose sugars.

8. The method of claim 7, wherein the enzymes comprise a mixture of cellulases and/or hemicellulases.

9. The method of claim 1, wherein the first period of time ranges from 1 hour to 48 hours.

10. The method of claim 1, wherein the oxidizing agent comprises an alkaline solution.

11. The method of claim 10, wherein the alkaline solution comprises NaOH and $H_2O_2$.

12. The method of claim 11, wherein the alkaline solution is mixed with the biomass at a NaOH-to-biomass ratio of 10 wt %, and a $H_2O_2$-to-biomass ratio of 12.5 wt %.

13. The method of claim 1, wherein the oxidizing agent is selected from the group consisting of: hydrogen peroxide, calcium hypochlorite, chlorine dioxide, ozone, potassium peroxymonosulfate, and ammonium persulfate.

14. The method of claim 1, wherein the second period of time ranges from 1 hour to 24 hours.

15. The method of claim 1, wherein the non-fermented LOX biomass is partially dried prior to being contacted with the ionic liquid.

16. The method of claim 1, wherein the non-fermented LOX biomass is filtered prior to being contacted with the ionic liquid.

17. The method of claim 1, wherein the ionic liquid comprises a cation selected from the group consisting of: imidazolium, pyrroldinium, pyridinium, phosphonium, and ammonium.

18. The method of claim 1, wherein the ionic liquid has the structural formula of Formula I:

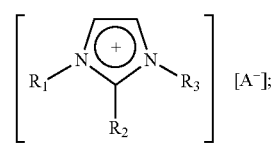

Formula I wherein:
each of $R_1$, $R_2$, and $R_3$ is independently hydrogen, an alkyl group having 1 to 8 carbon atoms, an alkoxy group having 1 to 8 carbon atoms, or an alkene group having 2 to 8 carbon atoms; and A is a halide, acetate, formate, dicyanamide, carboxylate, or phosphate anion.

19. The method of claim 18, wherein the alkyl group is substituted with sulfone, sulfoxide, thioether, ether, amide, or amine.

20. The method of claim 18, wherein the alkene group is an allyl or vinyl group.

21. The method of claim 18, wherein the halide is a chloride, fluoride, bromide, or iodide.

22. The method of claim 1, wherein the ionic liquid consists essentially of 1-ethyl-3-methylimidazolium acetate.

23. The method of claim 1, wherein the ionic liquid consists essentially of 1-n-butyl-3-methylimidazolium chloride.

24. The method of claim 1, wherein the ionic liquid comprises 1-allyl-3-methyl imidazolium chloride or allylimidazlium chloride.

25. The method of claim 1, wherein the ionic liquid consists essentially of 3-methyl-N-butylpyridinium chloride.

26. The method of claim 1, wherein the solvent is selected from the group consisting of: water, ethanol, methanol, and acetonitrile.

27. The method of claim 1, further comprising the step of washing the non-fermented LOXIL-treated biomass with a second solvent, wherein at least one of the cellulose component or the hemicellulose component is substantially insoluble in the second solvent, and the IL is substantially soluble in the second solvent.

28. The method of claim 27, wherein the washing fractionates and separates the cellulose component and the hemicellulose component.

29. The method of claim 27, wherein the second solvent is selected from the group consisting of: water, ethanol, methanol, and acetonitrile.

30. The method of claim 1, further comprising the step of recovering the IL by at least one of: distillation, membrane separation, solid phase extraction, or liquid-liquid extraction.

31. The method of claim 1, wherein the contacting of the non-fermented lignocellulosic biomass with the oxidizing agent comprises combining the biomass with an oxidizing solution at 10% (w/w) solids loading.

32. The method of claim 31, further comprising the step of mixing the combination of the non-fermented lignocellulosic biomass and oxidizing solution.

33. The method of claim 1, wherein the contacting of the solid with the ionic liquid comprises combining the solid with the ionic liquid at a range of from 5% to 20% (w/w) solids loading.

34. The method of claim 33, further comprising the step of mixing the combination of solid and ionic liquid.

* * * * *